(12) United States Patent
van Schelven et al.

(10) Patent No.: US 12,020,795 B2
(45) Date of Patent: Jun. 25, 2024

(54) SYSTEM AND METHOD FOR MEDICATION PREPARATION AND VERIFICATION

(71) Applicant: BLISTERPARTNER B.V., The Hague (NL)

(72) Inventors: Gijs van Schelven, The Hague (NL); Cornelis Verhagen, Heppen (BE); Loen van Zanten, The Hague (NL)

(73) Assignee: BLISTERPARTNER B.V., The Hague (NL)

( * ) Notice: Subject to any disclaimer, the term of this patent is extended or adjusted under 35 U.S.C. 154(b) by 680 days.

(21) Appl. No.: 17/011,209

(22) Filed: Sep. 3, 2020

(65) Prior Publication Data

US 2020/0402632 A1 Dec. 24, 2020

Related U.S. Application Data

(63) Continuation-in-part of application No. PCT/EP2019/055462, filed on Mar. 5, 2019.

(Continued)

(51) Int. Cl.
| | |
|---|---|
| *G16H 20/13* | (2018.01) |
| *A61J 1/03* | (2023.01) |
| *G06K 7/10* | (2006.01) |
| *G06K 7/14* | (2006.01) |
| *G06Q 10/0631* | (2023.01) |
| *G06Q 10/30* | (2023.01) |

(Continued)

(52) U.S. Cl.
CPC ............... *G16H 20/13* (2018.01); *A61J 1/03* (2013.01); *G06K 7/10366* (2013.01); *G06K 7/1413* (2013.01); *G06Q 10/06316* (2013.01); *G06Q 10/30* (2013.01); *G06T 7/20* (2013.01); *G09B 19/003* (2013.01); *G16H 40/67* (2018.01); *G16H 70/40* (2018.01); *G06T 2207/30196* (2013.01)

(58) Field of Classification Search
CPC ........ G16H 20/10; G16H 20/13; A61J 7/0069
USPC ........................................ 700/240
See application file for complete search history.

(56) References Cited

U.S. PATENT DOCUMENTS

| | | | |
|---|---|---|---|
| 5,408,443 A * | 4/1995 | Weinberger | A61J 7/0427 368/10 |
| 6,170,699 B1 | 1/2001 | Kim | |

(Continued)

OTHER PUBLICATIONS

International Search Report and Written Opinion corresponding to International Application No. PCT/EP2019/055462 mailed Jun. 5, 2019.

(Continued)

*Primary Examiner* — Gene O Crawford
*Assistant Examiner* — Ayodeji T Ojofeitimi
(74) *Attorney, Agent, or Firm* — Myers Bigel, P.A.

(57) ABSTRACT

A system for medication preparation and verification comprising: a device comprising a tray, a display, and at least one camera for capturing images of the tray; a database of medication information; and a controller, wherein the controller is configured to provide instructions on the display to a user regarding where to place a medication within compartments of the tray, control operation of the at least one camera for capturing images of the tray, automatically analyze the images captured by the camera, detect movement between the camera and the tray, and prevent release of medications from the tray until movement is no longer detected.

6 Claims, 10 Drawing Sheets

Related U.S. Application Data

(60) Provisional application No. 62/639,229, filed on Mar. 6, 2018.

(51) Int. Cl.
  *G06T 7/20* (2017.01)
  *G09B 19/00* (2006.01)
  *G16H 40/67* (2018.01)
  *G16H 70/40* (2018.01)

(56) References Cited

U.S. PATENT DOCUMENTS

| | | | |
|---|---|---|---|
| 6,449,921 B1 | 9/2002 | Kim | |
| 6,581,356 B2 | 6/2003 | Kim | |
| 6,585,132 B2 | 7/2003 | Kim | |
| 7,428,805 B2 | 9/2008 | Kim | |
| 8,452,446 B1* | 5/2013 | Madris | A61J 7/0084 |
| | | | 221/133 |
| 2008/0149657 A1* | 6/2008 | Kim | G01N 33/15 |
| | | | 221/2 |
| 2010/0147868 A1* | 6/2010 | Yuyama | G07F 17/0092 |
| | | | 221/97 |
| 2013/0018503 A1 | 1/2013 | Carson et al. | |
| 2015/0090733 A1* | 4/2015 | Park | A61J 7/0481 |
| | | | 221/277 |
| 2017/0305589 A1 | 10/2017 | Yuyama et al. | |

OTHER PUBLICATIONS

TCGRx Pharmacy Workflow Solutions: "TCGRx-Smart-TrayRx(TM)", Jan. 16, 2014 (Jan. 16, 2014), p. 1, XP054979413,Retrieved from the Internet:URL:https://www.youtube.com/watch?v=5KP1ZlcrzfO[retrieved on May 22, 2019].

TCGRx Pharmacy Workflow Solutions: "InspectRx—Inspect Pouches Efficiently and Accurately", Oct. 25, 2016 (Oct. 25, 2016), p. 1, XP054979409,Retrieved from the Internet:URL:https://www.youtube.com/watch?v=WSprhz1sTfc[retrieved on May 22, 2019).

"International Preliminary Report on Patentability corresponding International Application No. PCT/EP2019/055462 mailed Sep. 17, 2020".

* cited by examiner

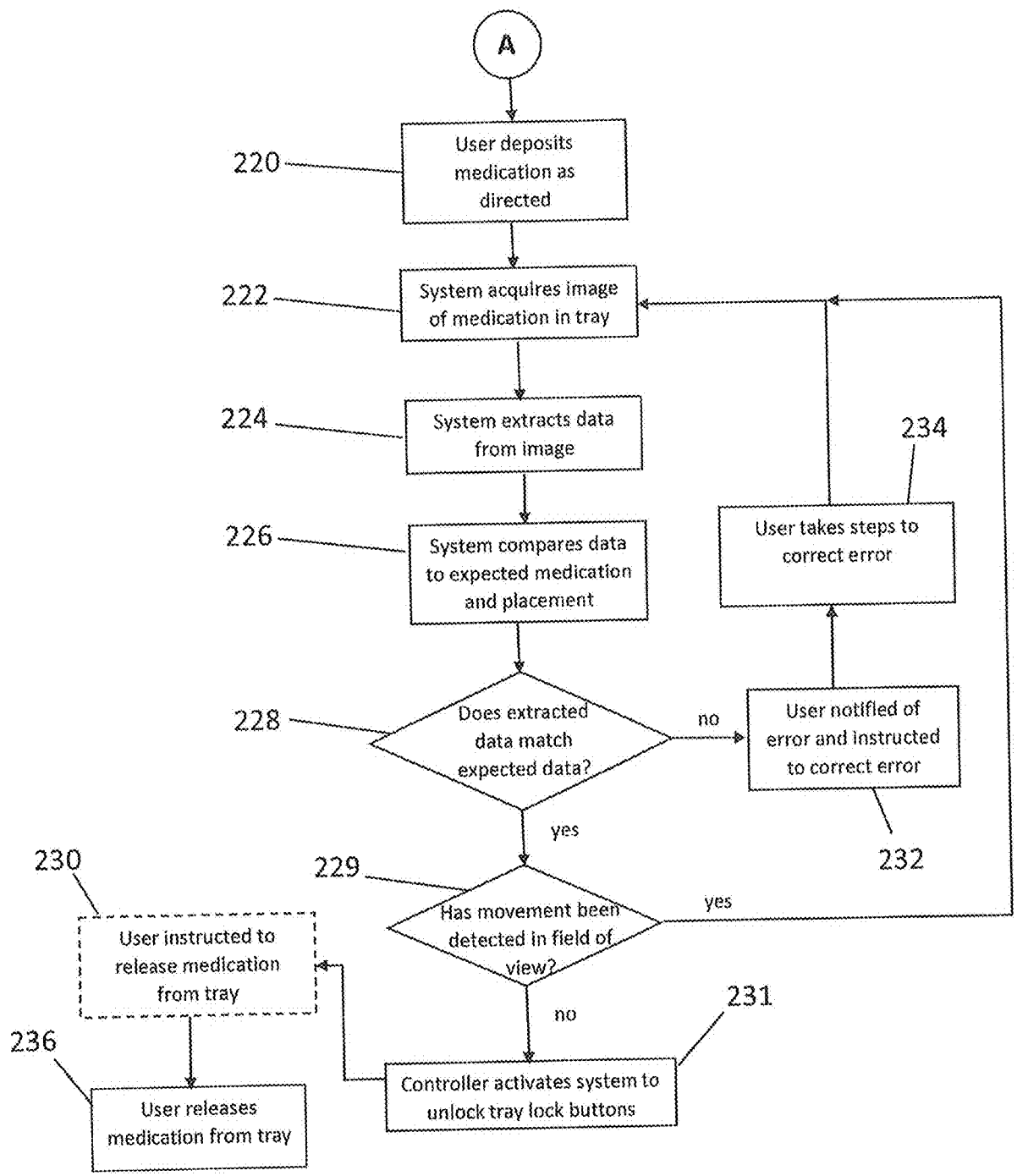

SYSTEM AND METHOD FOR MEDICATION PREPARATION AND VERIFICATION

RELATED APPLICATIONS

The present application is a continuation-in-part of PCT Application No. PCT/EP2019/055462; filed Mar. 5, 2019, which claims priority from and the benefit of U.S. Provisional Patent Application No. 62/639,229, filed Mar. 6, 2018, the disclosures of which are hereby incorporated by reference herein in full.

FIELD OF THE INVENTION

The present invention relates generally to the dispensing of prescriptions, and more particularly to automated dispensing of prescriptions.

BACKGROUND

Due to the increasing age of the population and the ever-increasing number of prescription medicines available, the demand for prescription drugs is growing at a rate that will far exceed the capacity and numbers of licensed pharmacists. The net impact of this imbalance is that pharmacists are increasingly spending more time doing clerical and administrative tasks such as verifying filled prescriptions and checking data entry done by pharmacy technicians. Since the capacity of any one pharmacist is fixed, the output of a pharmacy has become constrained.

This situation creates increased demands on a pharmacist's time and results in increased reliance on technicians and other non-professional staff to fill prescriptions, all creating an increased chance for prescription error. While these errors may take many forms, the likelihood of a dangerous or life-threatening "adverse drug event" increases proportionally with the increased chance of prescription fill error.

Some pharmacies may use automated packaging systems to create patient-specific compliance packages such as, for example, systems disclosed in U.S. Pat. Nos. 6,449,921; 6,585,132; and 7,428,805, the disclosures of which are hereby incorporated herein. Pills, tablets or capsules (sometimes referred to collectively as "tablets" herein) are held in bulk supply in these systems in canisters. The canisters are designed to cingulate, count and eject tablets for packaging into individual pouches of a strip upon command by the system controller. This type of packaging is most often used for adherence or compliance packaging where all of a patient's medications to be taken at a particular time (i.e., breakfast time, lunch time, dinner time, bedtime, or some other specified time of the day) are packaged into one pouch. It may also be used to create unit dose packaging where a single dose of a single medication is packaged in each pouch. This type of packaging may be used by individual patients, but also is commonly used in medical care facilities (i.e., nursing homes, group homes, hospitals, etc.), for emergency kits in these types of facilities, and for automated systems that dispense individual doses of medications, as well as other applications. Typically, pharmacies place their fastest-moving tablets into the canisters in these automated packaging systems in order to most efficiently fill prescription orders. Sometimes, however, a prescription order may require a pill that is not stored in a canister. As described in U.S. Pat. No. 7,428,805, referenced above, and further in U.S. Pat. Nos. 6,170,699 and 6,581,356, the disclosures of which are hereby incorporated herein, a manual dispensing tray may be used with the automated packaging unit. Tablets may be manually placed in compartment openings of a tray, the tray mounted on the packaging unit, and the tablets released from the tray compartments and packaged in pouches.

Although automated dispensing systems may be available, many prescription orders for oral solid medications are filled manually in pharmacies; that is, pharmacy staff may retrieve the appropriate stock bottle of medication from a shelf in the pharmacy, remove the appropriate number of medication units (e.g., pills, tablets, capsules, etc.) to fill the prescription, place them into the appropriate packaging to be provided to the patient, and then return the remaining pills to the stock bottle and the stock bottle to the shelf. Such a manual process may be followed for medications that are provided to the patient in a vial or bottle, but also for the preparation of patient-specific adherence or compliance packaging, such as blister packs or bingo cards, where the packaging consists of a grid of cavities, each cavity containing one or more medications for administration to the patient at a specific time (e.g., breakfast-time or morning dose, lunch-time or mid-day dose, dinner-time or afternoon dose, bedtime or evening dose, etc.) over a defined time period. This type of packaging is often used in nursing homes or other types of long-term care facilities, but also may be desirable for any patient who would like a simplified approach to medication administration. To prepare such types of compliance packaging, if more than one prescription is included, the pharmacy must align all prescriptions for the patient to determine the appropriate scheduling and assess whether there are any incompatibilities that require separate packaging of any of the medications in the order. Once a determination is made as to which medications will be packaged together for administration at the same time, the pharmacy staff may manually place the individual pills into the appropriate cavities of the card and then cover and seal the card, with appropriate labeling for each cavity/administration period. When more than one medication is included in the card, it is easy to imagine that getting the correct medication(s) into the correct package cavities may be an error-prone process.

Many existing pharmacy filling systems and procedures still require a human operator to visually validate whether the drug that is packaged for delivery to the customer is correct. Thus, the human factor can contribute to the majority of prescription fill errors. Existing visual verification techniques rely on comparing an electronic image of the prescribed medication, i.e., a picture of the prescribed medication retrieved from a data library, with the actual medication that is dispensed for the patient. Other systems and procedures rely on comparing the dispensed medication with that in the original manufacturer's supply container, or comparing an electronic image of the filled prescription with an electronic image of the prescribed medication retrieved from a data library. And, while automated inspection systems are known, they are typically used for inspection of pharmaceuticals prior to depositing in the packaging or final container, or after the pharmaceuticals have been placed in the packaging and the packaging has been sealed.

Each of these known manual verification and validation techniques typically requires that the pharmacist spend a significant portion of his day performing these administrative or clerical tasks and allows less time for patient consultation and other professional pharmacist activities. It may be desirable to enhance the flexibility of systems for preparation of prescription orders and automated verification of pharmaceuticals.

SUMMARY

As a first aspect, embodiments of the invention are directed to a system for medication preparation and verification comprising: a device comprising a tray, a display, and at least one camera for capturing images of the tray; a database of medication information; and a controller, wherein the controller is configured to provide instructions on the display to a user regarding where to place a medication within compartments of the tray, control operation of the at least one camera for capturing images of the tray, automatically analyze the images captured by the camera, detect movement between the camera and the tray, and prevent release of medications from the tray until movement is no longer detected.

As a second aspect, embodiments of the invention are directed to a method for medication preparation and verification comprising:

(a) receiving prescription order information, the prescription order information comprising one or more medications for a patient;
(b) displaying a list of the one or more medications on a display;
(c) selecting one of the displayed medications;
(d) retrieving a container with the selected medication from a location in the pharmacy;
(e) scanning the container;
(f) displaying an image of a tray and indicating compartments in the tray in which individual units of the medication should be deposited;
(g) depositing units of medication as instructed on the display;
(h) capturing one or more images of the tray with the medication units;
(i) extracting data from one or more of the captured images;
(j) comparing the extracted data to analogous data for the selected medication, the analogous data stored in a medication database;
(k) detecting whether movement is present above the compartments; and
(l) releasing medications from the tray after movement is no longer detected above the tray and a positive comparison of extracted data and analogous data is achieved.

As a third aspect, embodiments of the invention are directed to a system for medication preparation and verification comprising: a device employed in filling prescriptions, the device including a scanner for scanning medication containers; a waste receptacle; means for detecting entry of a container into the waste receptacle; a database of medication information; and a controller operatively associated with the device, the database and the means for detecting entry of a container, wherein, when the entry of a first container into the waste receptacle is detected, the controller is configured to require scanning of a second container with the scanner prior to permitting filling of prescriptions with the device.

BRIEF DESCRIPTION OF THE FIGURES

FIGS. 6A, 6B and 6C are flow charts illustrating operations of verification systems according to embodiments of the invention.

DESCRIPTION

Figure 1:
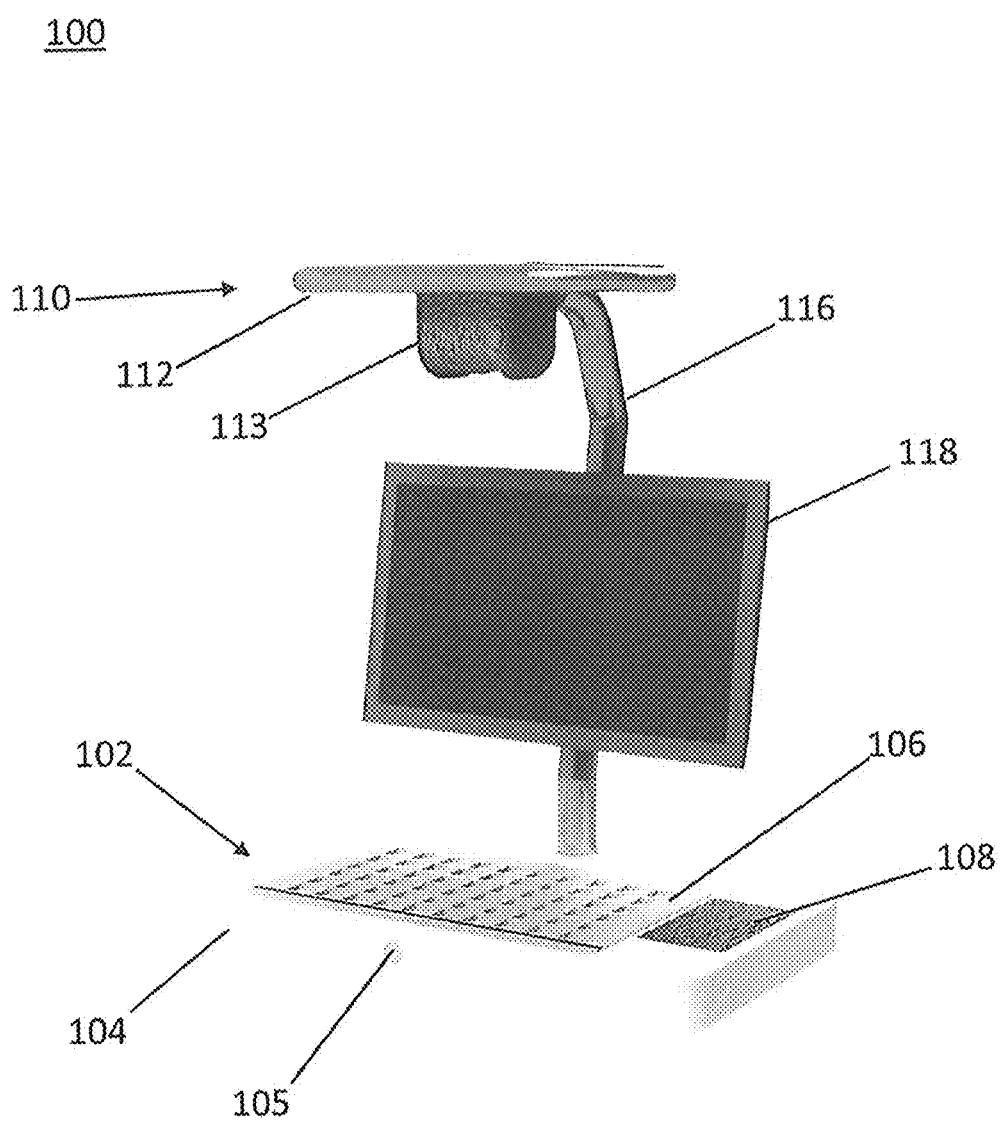
FIG. 1 is a perspective view of a system for verifying pharmaceuticals according to embodiments of the invention.

The present invention will now be described more fully hereinafter, in which embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. In the drawings, like numbers refer to like elements throughout. Thicknesses and dimensions of some components may be exaggerated for clarity.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein the expression "and/or" includes any and all combinations of one or more of the associated listed items.

In addition, spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. The device may be otherwise oriented (rotated 90 degrees or at other orientations) and the spatially relative descriptors used herein interpreted accordingly.

As described above, the invention relates generally to a system and process for verifying pharmaceuticals in preparation for packaging. An exemplary device as used in the system is shown in FIG. 1 and designated broadly therein at 100. The device 100 includes a base 102, a vertical support 116, and an image-capture portion 110. The base comprises a platform 104, a tray 106, a work area 108 on the upper surface of the platform 104, and a button 105. The device 100 may include an indicia reader such as an RFID reader or barcode scanner (not shown). The indicia reader may be located in any reasonable location on the device 100 but may, for example, be incorporated into the base 102. The indicia reader may be used for reading indicia on a manual dispensing tray for an automated packager, on blister cards, on identification tags for pharmacy staff, on stock bottles or other medication packaging, etc. The device 100 additionally includes a display 118 for displaying information to the user from a system controller (not explicitly shown, but described below) such as prescription order information, medication information, packaging instructions and verification results. Alternatively, the display 118, or an additional display, may be separate from the device 100 but in communication with the system to display the same types of information.

Figure 2:
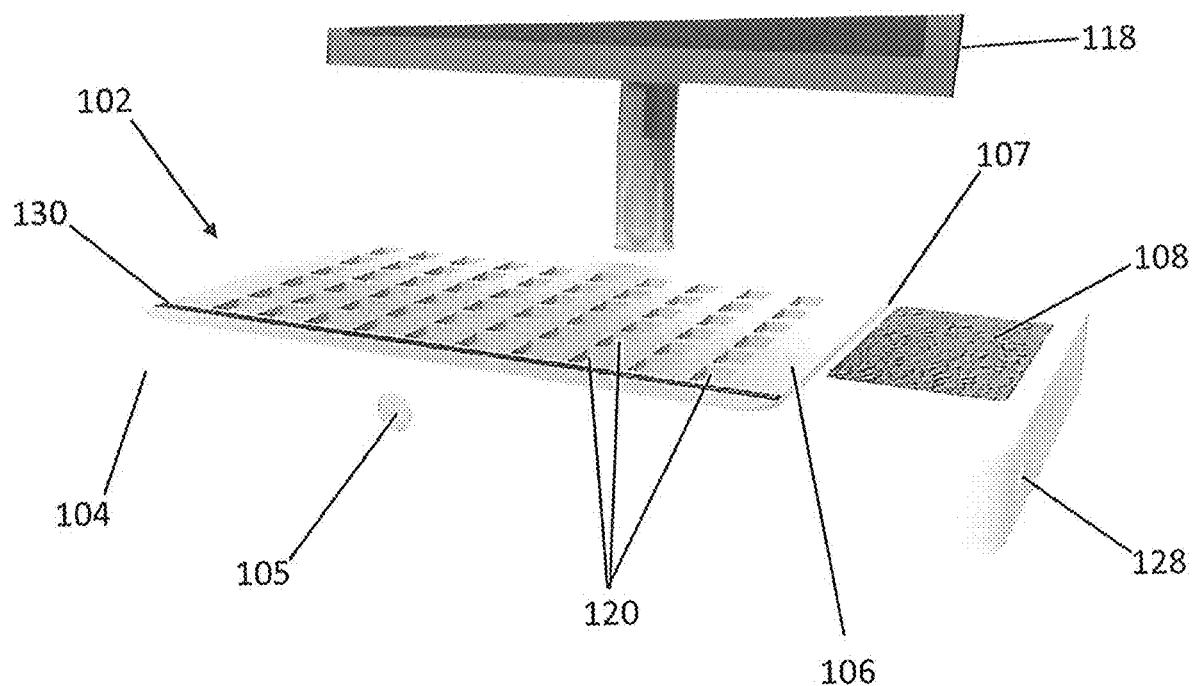
FIG. 2 is an enlarged partial perspective view of the system of FIG. 1.

Turning now to FIG. 2, the tray 106 sits within a recess 107 of the platform 104 and is divided into compartments 120, which are through-holes in the tray 106. The tray 106 may include a stripe 130 or other marking that may be used in the verification process to facilitate detection of activity by one or more cameras 114, 115 in the camera housing 113 (see FIG. 5). The tray 106 may be provided in various configurations to accommodate a variety of formats of blister cards that may be preferred to be used with the device 100.

Figure 3:
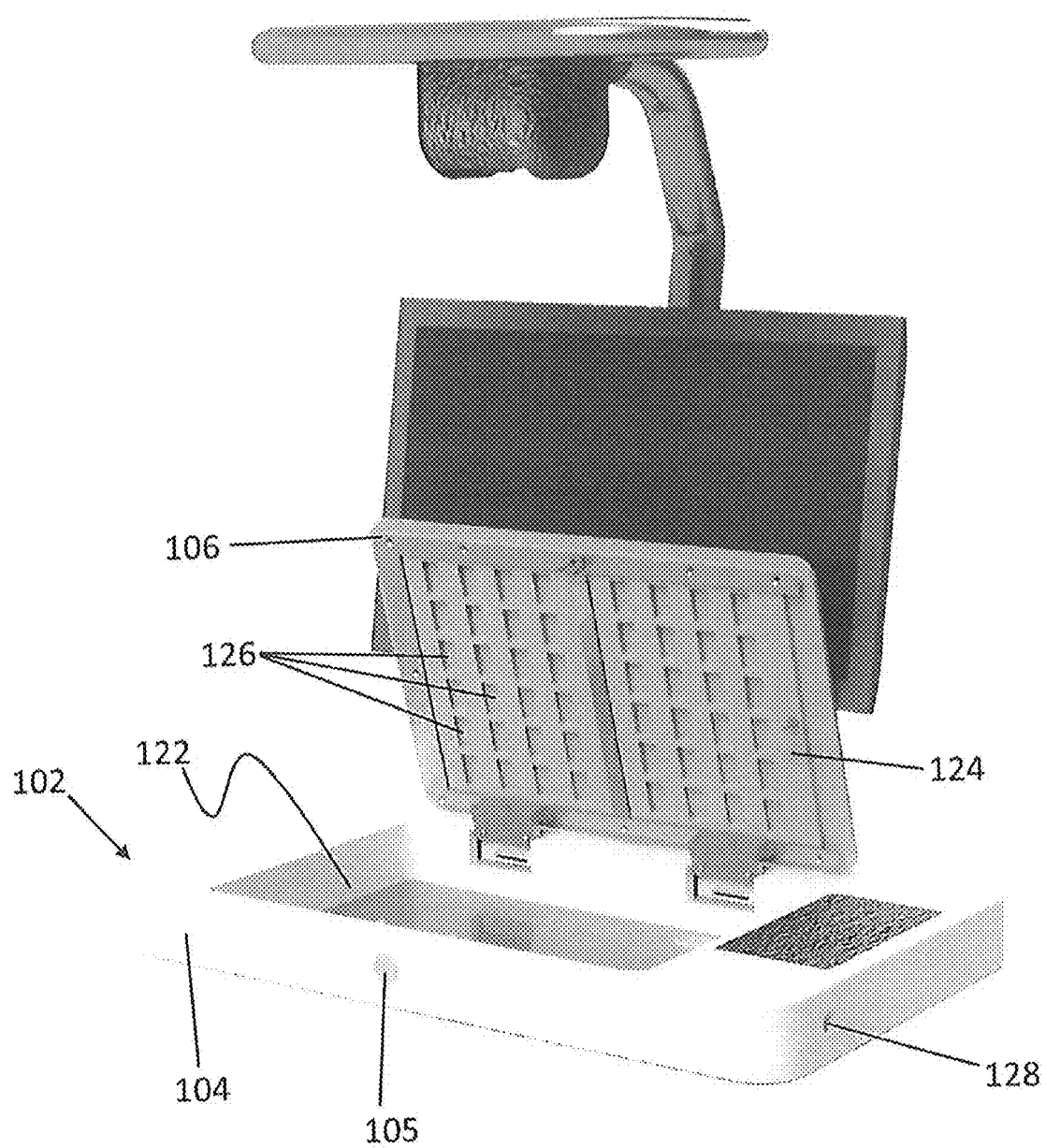
FIG. 3 is a perspective view of the system of FIG. 1 with the tray in an open position and the movable screen positioned to close the compartments of the tray.

The tray 106 may be movably attached to the platform 104. As shown in FIG. 3, the tray 106 may be opened by movement on hinges and secured in place with a latch 125 when closed; a button 105 may be depressed to release the latch 125 so that the tray 106 can be moved to the open position. Alternatively, the tray 106 may be unattached and entirely removable from the recess 107 or the tray 106 may be permanently attached to the platform 104. The platform 104 includes an open space 122 below the recess 107. One or more blister cards or a manual dispensing tray for an automated packaging unit may be placed into the space 122; this may be accomplished by removing the tray 106 from the recess 107, placing the blister card(s) or manual dispensing tray in the space 122, and replacing the tray 106 in the recess 107. Alternatively, an opening may be provided in a side of the platform 104 allowing access to the space 122, and the manual dispensing tray or blister card(s) may be inserted through the opening into the space 122 below the recess 107. In either case, the result is that, when the tray 106 is positioned in the recess 107, the tray 106 rests above the blister card(s) or manual dispensing tray, and the compartments 120 of the tray 106 are aligned with the locations of the cavities of the blister card(s) or the compartment openings of the manual dispensing tray.

Figure 4:
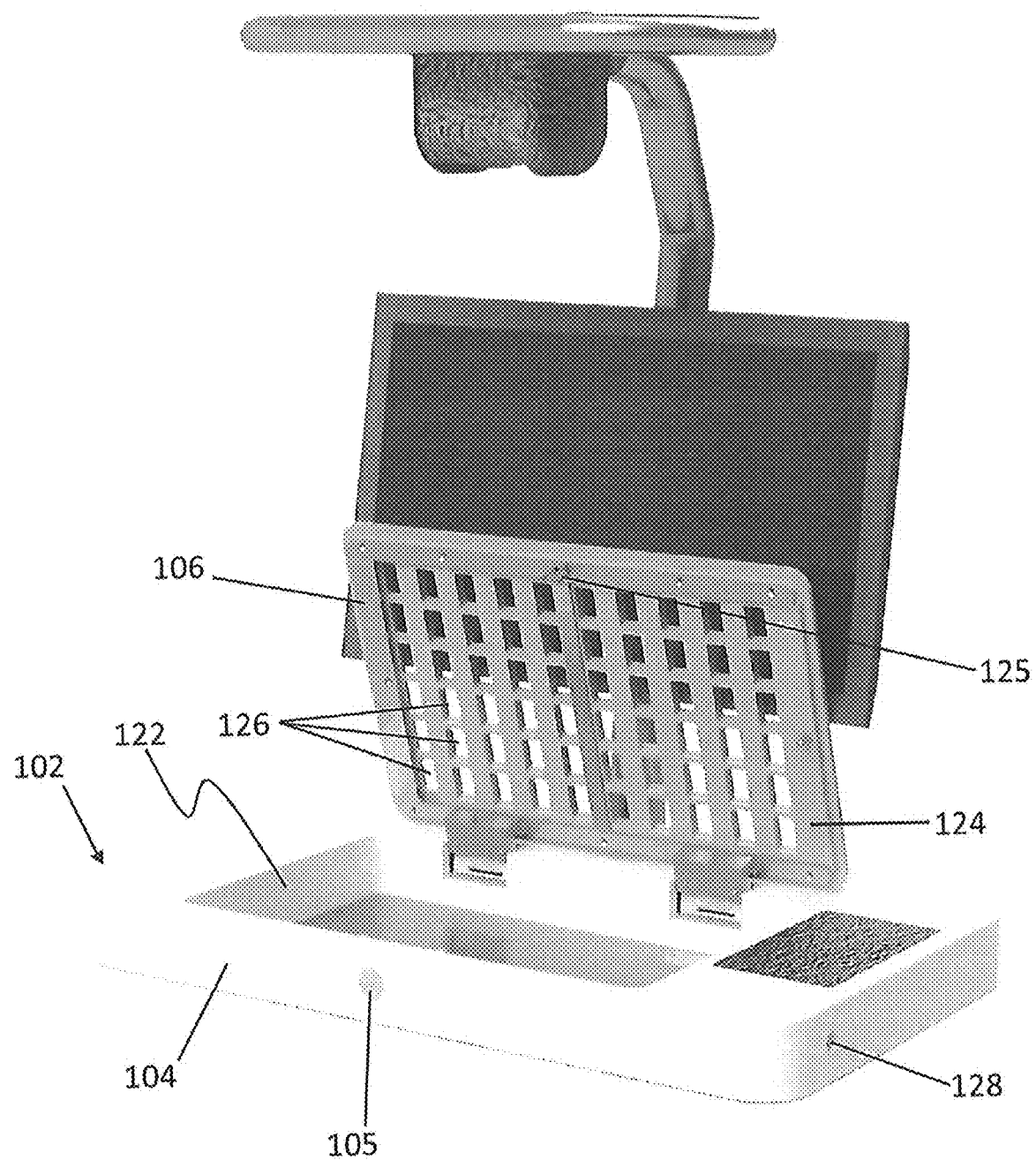
FIG. 4 is a perspective view of the system of FIG. 1 with the tray in an open position and the movable screen positioned to open the compartments of the tray.

The tray 106 also may include one or more movable screens 124 below the compartments 120. The movable screen 124 may comprise a single sheet with openings 126 therein that are sized and spaced to align with the compartments 120 of the tray 106. When the movable screen 124 is in the open position (FIG. 4), the openings 126 are aligned with the compartments 120 of the tray 106, thereby allowing items deposited in the compartments 120 to pass out of the tray 106. The movable screen 124 may be moved from this position by sliding side-to-side or front-to-back. Prior to use, the movable screen 124 may be positioned such that the openings 126 are no longer aligned with the compartments 120 of tray 106 (in this example, the movable screen 124 is slid to the left; FIG. 3), thereby closing the compartments 120 and allowing the tray 106 to retain any items deposited in the compartments 120. Alternatively, there may be one movable screen 124 per compartment 120, or multiple movable screens 124, each encompassing a subset of the compartments 120. If more than one member 124 is present, the members 124 may be individually movable or may be operated in concert. The movable screens 124 may move by sliding, as shown herein, by swinging on a hinge, or in any other fashion as appropriate for the tray 106 and platform 104 design. The transition of the movable screen 124 between a closed and open position may be performed manually by having the user depress one or more buttons 128, slide a lever, or use another appropriate manual mechanism. Alternatively, the movement of the movable screen 124 may be automatically controlled by the system.

Figure 5:
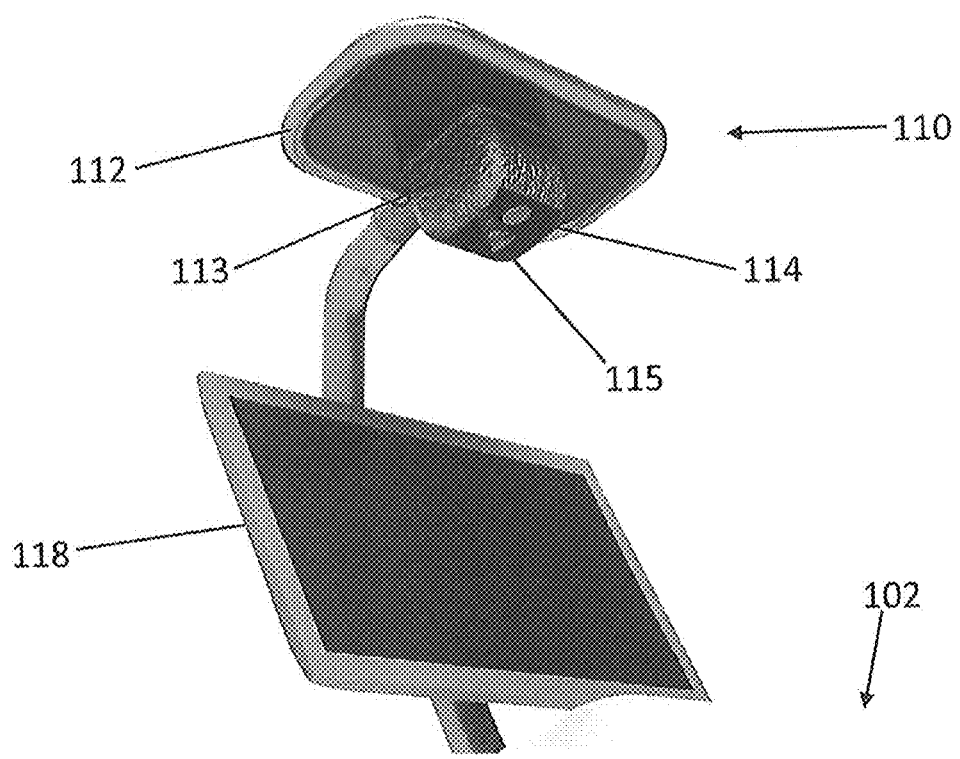
FIG. 5 is a bottom partial perspective view of the system of FIG. 1 showing the display and camera.

Referring now to FIG. 5, the image-capture portion 110 of the device 100 includes a light frame 112 and a camera housing 113. The light frame 112 supports the mounting of lights that are used to illuminate the base 102 for image acquisition. The camera housing 113 accommodates one or more cameras 114, 115 that are used for image acquisition; the cameras 114, 115 may be video cameras or may capture static images. At least one camera 114 is mounted in the housing 113 and aimed in the direction of the tray 106; camera 114 captures images of tablets placed in the tray 106 for use during the verification process. Another camera 115 may be mounted in the housing 113 and aimed in the direction of the work area 108. Either or both of cameras 114, 115 may capture video and/or static images of activity that occurs during the package preparation process, including but not limited to movement of the user's hands. Such movement of the user's hands may include, without limitation, activities such as loading medication into the compartments 120 of the tray 106, removing medication from the compartments 120 of the tray 106, scanning of stock bottles, depositing empty stock bottles into a trash receptacle, etc. The user's hands and movements also may be displayed on the display 118 in real time. During the verification process, cameras 114, 115 may be used to read the bar code on the stock bottle or original packaging for the medication used to fill the prescription. Cameras 114, 115 may also or instead be used to capture an image of the label on the stock bottle or original packaging for the medication. The label image may be used as part of the verification process by comparison to a database of medication labels.

The system also includes a database comprising information about prescription medications, including but not limited to medication name, NDC number, size, color, imprints, markings, etc. The database also may include information about nonprescription items such as over-the-counter medications (i.e., antihistamines, pain relievers, anti-inflammatory medications, etc.), vitamins, supplements, etc. These nonprescription medications may also be prepared for packaging and verified using the system and steps described herein for prescription medications would apply to these items as well, mutatis mutandis. The system may include a database of medication label information (i.e., label image information) that may be used to identify medication containers.

Any or all of the components described above may be controlled by an automated controller. The function of an exemplary controller and associated hardware, software and the like is discussed below.

Figure 6A:
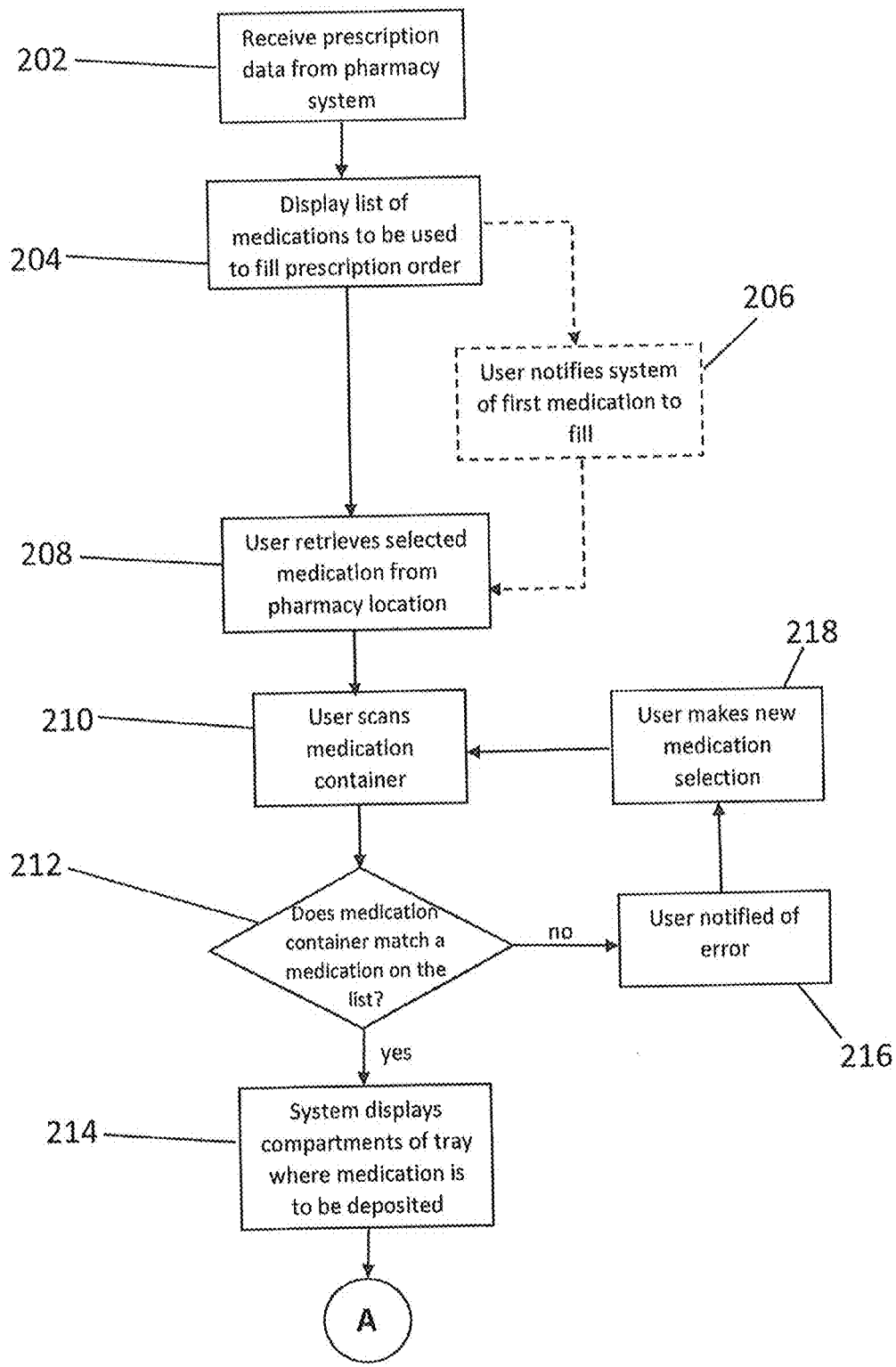
Figure 7:
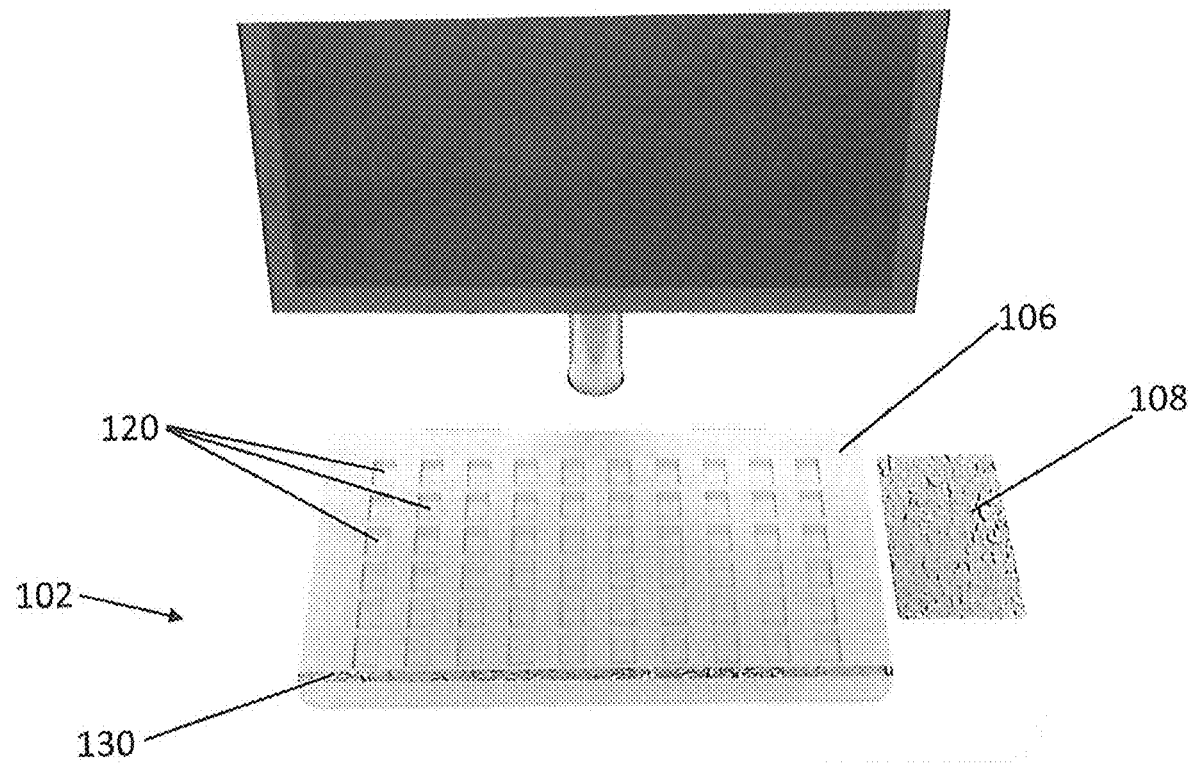
FIG. 7 is a front perspective view of the system of FIG. 1 with the tray in a closed position and the movable screen positioned to close the compartments of the tray.

Turning now to FIGS. 6A and 6B, the process for package preparation and verification will now be described with reference to the preparation of blister cards. The same steps are applicable, mutatis mutandis, for the preparation of manual filling trays for automated packagers. The process begins with the movable screen 124 positioned so that the openings 126 are not aligned with the compartments 120; the compartments 120, then, are closed and able to retain items in them (FIG. 7). At step 202 the verification system receives information regarding a prescription order to be filled for a patient from the pharmacy management system. A prescription order may include one or more prescriptions for that patient. If the prescription order includes more than one prescription, at this point it may have already been determined which medications will be packaged together; alternatively, the system may make this determination. In either case, the system may display all medications to be packaged at step 204 and at step 206 the user may select from the list the first medication that he/she wishes to package. At step 208 the user retrieves the medication from its location in the pharmacy. Optionally, the system may tell the user where to find the medication in the pharmacy and may do so by displaying a diagram of the pharmacy with the location of the medication highlighted. At step 210, the user may scan the medication container to confirm that the correct medication container has been retrieved. This may be done using the cameras 114, 115 and may be accomplished when the medication container is placed in the work area 108 (by imaging the container barcode and/or label, as discussed above). Alternatively, an auxiliary barcode scanner may be attached to and/or in communication with the system. Scanning the medication container also may be accomplished automatically if the container includes an RFID tag and the system includes an RFID reader. At step 212 the system may determine if the retrieved medication matches the medication selected to be packaged. If there is a match, the system may instruct the user at step 214 where to place individual units of the medication (and how many units) by displaying an image of the tray 106 (real-time video, real-time still image, or the like) on the display 118 and highlighting the compartments 120 to be filled. Highlighting of the compartments 120 on the image of the tray 106 shown on the display 118 may include, without limitation, a particular color, pattern, outline or other indicator (e.g., arrow) of each compartment 120 to which the pill(s) are to be placed. If more than one pill is to be placed into a particular compartment 120, the display may indicate this by showing the numerical representation or other representation of the number of pills within the displayed image representing that compartment 120 (e.g., for two pills, a double outline or two arrows).

If the selected medication and the retrieved medication container do not match, the system may alert the user at step 216 and at step 218 the user may correct the error by selecting a new medication container from a location in the pharmacy.

An alternative workflow may not include step 206. The user may simply choose a medication from the list, retrieve the appropriate medication container in the pharmacy, and image/scan the container for confirmation of the drug (steps 208, 210 and 212). If the retrieved drug is on the list medications to be packaged (step 204), then that medication is identified as the selected medication to be packaged and the system proceeds to step 214 to instruct the user where to place the selected medication. If the retrieved drug is not on the list of medications to be packaged, the system may alert the user to the error and instruct the user to correct the error.

Figure 8:
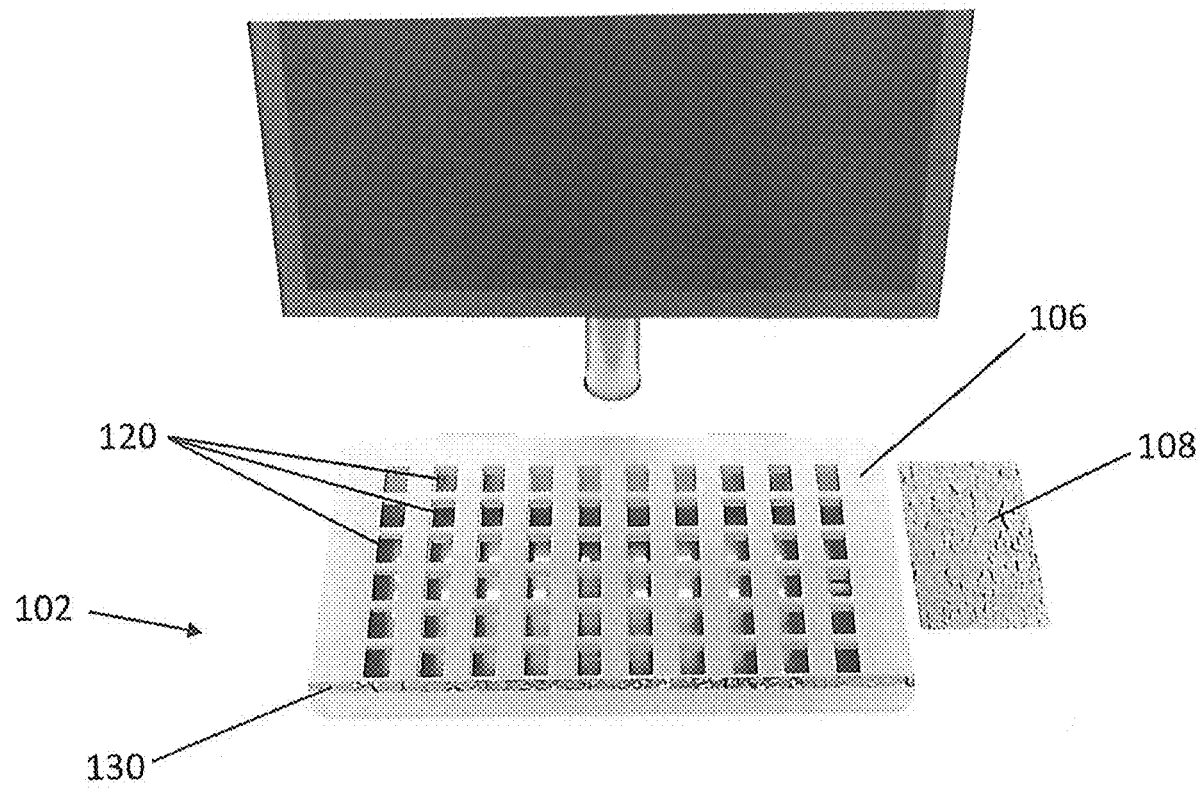
FIG. 8 is a front perspective view of the system of FIG. 1 with the tray in a closed position and the movable screen positioned to open the compartments of the tray.

At step 220, the user deposits the indicated number of units of medication in each of the selected compartments 120 of the tray 106, as directed on the display 118. At step 222, if the cameras 114, 115 no longer detect the user's hands in the field of view, the system acquires an image of the medication in the tray and at step 224 extracts data from the acquired image. At step 226 the system compares the extracted data to analogous data for the selected medication (expected data) and determines if there is a match at step 228. The data that may be analyzed may include, but not be limited to, pill size, shape, color, markings, imprints, and the number of pills in the compartment. The analysis may be performed in real time and the system may indicate the result in real time, for example, by changing a color or other visual attribute on the display (e.g., green for a positive match, red for a negative match). Alternatively, the system may wait until pills have been placed in all designated compartments 120 to perform the data analysis. If the data match, the user is instructed at step 230 to release the medication from the tray 106, such as by depressing a button 128, sliding a lever, or other mechanism to move the movable screen 124 and align the openings 126 with the compartments 120 (FIG. 8). As a safety precaution, the system may include more than one button 128 (i.e., one on each side of the base 102), requiring both buttons to be depressed simultaneously in order to avoid accidental release of the medications from the tray 106. Alternatively, the system may be designed to automatically release the contents of the tray 106 upon a positive match.

The system may provide additional security such that every time the user's hands are detected by the cameras 114, 115, the buttons 128 are inactivated and the movable screen 124 locked in position so that the pills may not be released until another inspection is successfully completed. This query is shown at step 229 in FIG. 6B. Once the system again inspects the pills, if all compartments 120 of the tray 106 pass the inspection, and there has been no movement detected, the buttons 128 will be activated (step 231) so that the user can depress the buttons 128, sliding the movable screen 124 aside and releasing the pills to the blister card below (step 236). This process may be repeated every time activity is detected in the field of view of cameras 114, 115 to ensure that no changes have been made to the contents of the compartments 120 after the inspection and before the pills are released to the blister card. Optionally, the system may instruct the user to release the pills (step 230).

If the extracted data does not match the expected data at step 228, the user may be notified of the error at step 232 and take measures to correct the error at step 234. Corrective steps may include, for example, adjusting the number of pills in one or more compartments 120 of the tray 106, removing pills from certain compartments 120 of the tray 106, adding pills to empty compartments 120 of the tray 106, removing all pills from the tray and retrieving a different medication container, etc. In the case of an error, the system may take steps to prevent the user from being able to release the contents of the tray (i.e., by inactivating the buttons 128, locking the position of the movable screen 124, or any other such action as may be appropriate to the design).

This process is repeated for all medications required for the prescription order and may be performed separately for each pill in the prescription or may be performed for multiple pills in the compartments 120 at one time. When all medications have been distributed in the tray 106, verified, and released into the blister card below the tray 106, the blister card is removed from the device 100. A label for the blister card is then placed over the card and attached to the card (i.e., sealed using a method such as a heating device or adhesive, for example). Typically, the label may include patient information (such as, for example, patient name, address or room number, physician name, patient identification number, etc.), prescription information (such as, for example, prescription number(s), medication name(s), medication dosage, NDC number(s), administration day/time for each cavity of the blister card, warnings or special instructions, etc.), and pharmacy information (such as, for example, pharmacy name, address, phone number, pharmacist name, etc.). The blister card is then ready for distribution to the facility or patient.

Figure 6C:
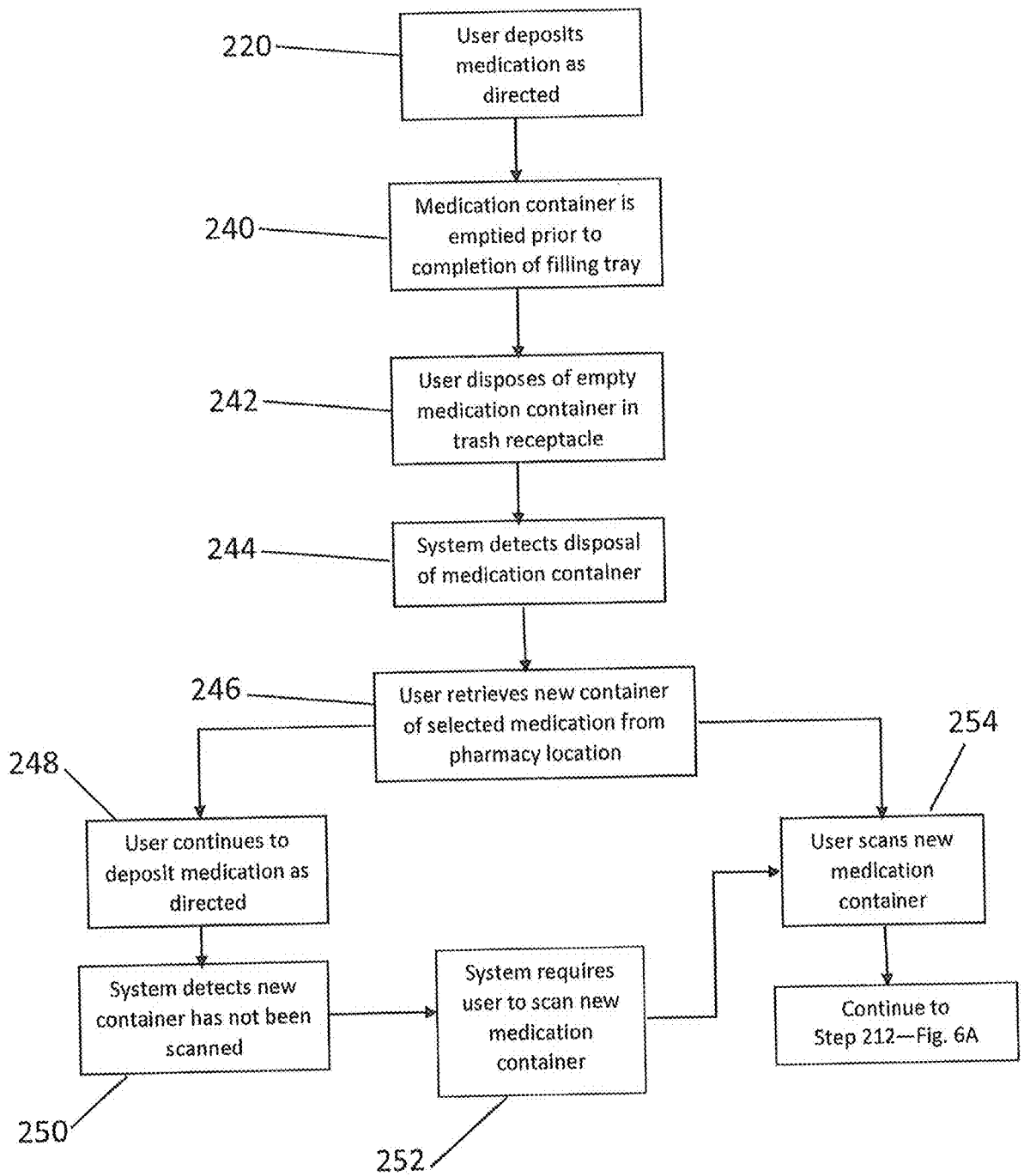

Referring now to FIG. 6C, during the process of packaging the medication, the user may empty the contents of a particular stock bottle that has been scanned and confirmed for filling of the prescription (step 240 in FIG. 6C). If additional units of that medication are required to complete the filling of the blister card, it is critical that the user scan the new stock bottle prior to use to confirm that it also contains the correct drug and dosage. Additionally, it is important for the system to record the new expiration date for the new stock bottle, as well as track the lot number in the case of a drug recall. This scan can additionally be advantageous for tracking drug inventory within the pharmacy. This step of scanning the new bottle, however, is one that can be easily skipped by the user. In some embodiments, the system may include additional security features that force compliance with this step. The workstation location for the device 100 may include a trash receptacle for disposal of the empty stock bottle. The trash receptacle may include a sensor that detects disposal of the stock bottle. Alternatively, or additionally, the trash receptacle may be in the field of view of cameras 114, 115 and cameras 114, 115 may monitor disposal of stock bottles. When disposal of a stock bottle (step 242) is detected by any means (step 244), the system may require the user to scan a new stock bottle (step 254) prior to proceeding with filling of the tray 106. As above, if an incorrect stock bottle is scanned for the required medication, or if the scanning of the second container is not performed (steps 248 and 250), the system will notify the user of the error (step 252) and instruct the user to select and scan the correct stock bottle (step 254) before allowing the user to proceed with further filling of the tray 106.

If the system is used to fill a manual filling tray for an automated packager, once all medications in the prescription order have been loaded and verified by the system, the tray is removed from the device 100 and transferred to the automated packager for packaging.

In some embodiments, information (including video or images) collected during the various process steps may be archived or otherwise stored for subsequent review or auditing. In some embodiments, the system may include indicators, such as, for example, LED lights, on the tray 106 to additionally guide the user in placing the appropriate pills in the appropriate compartments 120 of the tray 106 according to the prescription. The controller may control the color, on/off state, or other state (i.e., blinking, solid, etc.) in accordance with the prescription to direct the user to the correct compartment(s) 120 when placing each pill.

The present invention has been described herein with reference to flowchart and/or block diagram illustrations of methods, systems, and devices in accordance with exemplary embodiments of the invention. It will be understood that each block of the flowchart and/or block diagram illustrations, and combinations of blocks in the flowchart and/or block diagram illustrations, may be implemented by computer program instructions and/or hardware operations. These computer program instructions may be provided to a processor of a general purpose computer, a special purpose computer, or other programmable data processing apparatus to produce a machine, such that the instructions, which execute via the processor of the computer or other programmable data processing apparatus, create means for implementing the functions specified in the flowchart and/or block diagram block or blocks.

These computer program instructions may also be stored in a computer usable or computer-readable memory that may direct a computer or other programmable data processing apparatus to function in a particular manner, such that the instructions stored in the computer usable or computer-readable memory produce an article of manufacture including instructions that implement the function specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions that execute on the computer or other programmable apparatus provide steps for implementing the functions specified in the flowchart and/or block diagram block or blocks.

It will be further appreciated that the functionality of any or all of the program modules may also be implemented using discrete hardware components, one or more application specific integrated circuits (ASICs), or a programmed digital signal processor, controller or microcontroller. The program code may execute entirely on a single processor and/or across multiple processors, as a stand-alone software package or as part of another software package. The program code may execute entirely on an electronic device or only partly on the electronic device and partly on another device. In the latter scenario, the other device may be connected to the electronic device through a wired and/or wireless local area network (LAN) and/or wide area network (WAN), or the connection may be made to an external computer (for example, through the Internet using an Internet Service Provider).

The foregoing embodiments are illustrative of the present invention, and are not to be construed as limiting thereof. Although exemplary embodiments of this invention have been described, those skilled in the art will readily appreciate that many modifications are possible in the exemplary embodiments without materially departing from the novel teachings and advantages of this invention.

What is claimed is:

1. A system for medication preparation and verification comprising:
    a device comprising a tray, a display, and at least one camera for capturing images of the tray;
    a database of medication information;
    a controller, wherein the controller is configured to provide instructions on the display to a user regarding where to place a medication within compartments of the tray, control operation of the at least one camera for capturing images of the tray, automatically analyze the images captured by the camera, detect movement between the camera and the tray, and prevent release of medications from the tray until movement is no longer detected.

2. The system of claim 1 wherein providing the instructions comprises highlighting the compartments on a diagram of the tray.

3. The system of claim 1, wherein the tray has compartments for storing items placed therein; wherein the device includes one or more movable screens, the one or more movable screens preventing release of the items from the compartments when in a closed position, and allowing release of the items from the compartments when in an open position; and wherein, when the controller determines that movement is no longer detected, the system permits relocation of the screen relative to the compartments to release the medications.

4. The system of claim 1 wherein automatically analyzing comprises automatically extracting data from the captured images about medication in the compartments of the tray and comparing the extracted data to data stored in the database for an expected medication.

5. The system of claim 4 wherein the expected medication is the medication that the controller has instructed the user to place in the compartments.

6. The system of claim 5 wherein, if the comparing results in a match of the extracted data and the data for the expected medication, the controller instructs the user to release the medication from the tray and, if the comparing does not result in a match of the extracted data and the data for the expected medication, the controller notifies the user of an error.

* * * * *